(12) United States Patent
Palmer et al.

(10) Patent No.: US 6,589,265 B1
(45) Date of Patent: Jul. 8, 2003

(54) INTRASACCULAR EMBOLIC DEVICE

(75) Inventors: Olin J. Palmer, Mountain View, CA (US); Jeff Krolik, Campbell, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 225 days.

(21) Appl. No.: 09/704,136

(22) Filed: Oct. 31, 2000

(51) Int. Cl.⁷ .......................... A61M 29/00; A61F 2/06
(52) U.S. Cl. ........................ 606/200; 623/1.1
(58) Field of Search .................. 606/200, 151; 623/1.1, 1.2

(56) References Cited

U.S. PATENT DOCUMENTS

| 5,192,301 | A | 3/1993 | Kamiya et al. |
|---|---|---|---|
| 5,350,398 | A | 9/1994 | Pavcnik et al. |
| 5,556,413 | A | 9/1996 | Lam |
| 5,733,294 | A | 3/1998 | Forber et al. |
| 5,792,154 | A | 8/1998 | Doan et al. |
| 5,843,118 | A | 12/1998 | Sepetka et al. |
| 5,846,261 | A | 12/1998 | Kotula et al. |
| 5,853,422 | A | 12/1998 | Huebsch et al. |
| 5,911,731 | A | 6/1999 | Phan et al. |
| 5,916,235 | A | 6/1999 | Guglielmi |
| 5,925,060 | A | 7/1999 | Forber |
| 5,925,062 | A | 7/1999 | Purdy |
| 5,928,260 | A | 7/1999 | Chin et al. |
| 5,935,148 | A | 8/1999 | Villar et al. |
| 6,036,720 | A | 3/2000 | Abrams et al. |
| 6,063,070 | A | 5/2000 | Eder |
| 6,086,577 | A | 7/2000 | Ken et al. |
| 6,126,672 | A | 10/2000 | Berryman et al. |
| 6,136,015 | A | 10/2000 | Kurz et al. |
| 6,139,564 | A | 10/2000 | Teoh |
| 6,149,664 | A | 11/2000 | Kurz |
| 6,152,144 | A | 11/2000 | Lesh et al. |
| 6,156,061 | A | 12/2000 | Wallace et al. |
| 6,159,165 | A | 12/2000 | Ferrera et al. |
| 6,159,206 | A | 12/2000 | Ogawa |
| 6,165,178 | A | 12/2000 | Bashiri et al. |
| 6,165,193 | A | 12/2000 | Greene, Jr. et al. |
| 6,168,592 | B1 | 1/2001 | Kupiecki et al. |
| 6,168,615 | B1 * | 1/2001 | Ken et al. ............ 623/1.1 |
| 6,168,622 | B1 | 1/2001 | Mazzocchi |
| 6,171,326 | B1 | 1/2001 | Ferrera et al. |
| 6,178,968 | B1 | 1/2001 | Louw et al. |
| 6,187,024 | B1 | 2/2001 | Boock et al. |
| 6,187,027 | B1 | 2/2001 | Mariant et al. |
| 6,190,373 | B1 | 2/2001 | Palermo et al. |
| 6,190,402 | B1 | 2/2001 | Horton et al. |
| 6,346,117 | B1 * | 2/2002 | Greenhalgh ............ 606/200 |
| 6,428,558 | B1 * | 8/2002 | Jones et al. ............ 606/200 |

FOREIGN PATENT DOCUMENTS

GB 1205743 9/1970

* cited by examiner

*Primary Examiner*—Peter Nerbun
(74) *Attorney, Agent, or Firm*—Fulwider Patton Lee & Utecht, LLP (57) ABSTRACT

An intrasaccular device particularly adapted for treating body lumens. The intrasaccular device includes structure that provides a strong framework as well as improved covering across an opening to an aneurysm sac. The intrasaccular device is intended to retain foreign bodies within the aneurysm sac and includes members for accomplishing this objective. The intrasaccular device is also provided with structure that facilitates the alignment of a plurality of devices deployed within the sac.

15 Claims, 6 Drawing Sheets

INTRASACCULAR EMBOLIC DEVICE

BACKGROUND OF THE INVENTION

The present invention relates to intravascular repair methods and devices for treating hollow spaces such as aneurysms, fistulas, and other cavities and lumens within a patient's body, and is particularly suited for the treatment of intra-cerebral aneurysms of the cerebral vasculature.

The use of intravascular devices for the treatment of aneurysms has received an increasing amount of attention in the past several years as both the methods and devices available for intravascular procedures have become more efficacious. One such method involves the insertion of a foreign body, such as an occlusion coil, within the aneurysm to precipitate the formation of a clot or thrombus to thereby partially or completely occlude the aneurysm and seal off the aneurysm. This method typically poses the risk of the coil or ensuing thrombus migrating from the aneurysm to the parent artery and causing an undesired blockage. This method is also often limited to the treatment of aneurysms with small necks opening into the artery in order to ensure that the foreign body will remain within the aneurysm.

In another approach, a plug is inserted into the neck of a saccular aneurysm to block off blood flow into the aneurysm. If the plug is not sized correctly it may dislodge from the aneurysm and into the patient's vasculature. In addition, placement of such a plug necessitates robust contact with the aneurysm, which can cause rupture of the aneurysm and hemorrhaging.

Attempts have also been made to treat both saccular and fusiform aneurysms by deploying grafts within the vasculature and anchoring them on either side of the aneurysm. These grafts typically extend along the entire length of a fusiform aneurysm, or lie across the mouth of a saccular aneurysm, thereby completely blocking off the flow of blood to the aneurysm and relieving the pressure thereon.

Such graft devices may consist of a tube adapted to be disposed across an aneurysm and having a wire woven into one end of the graft that can be expanded to sealingly engage the vessel wall. The tube is preferably made of a suitable polyester material. In yet another approach to the problem, a sheet of resiliently flexible biocompatible material may be employed. The sheet is rolled upon itself about one of its longitudinal edges and is introduced adjacent to the aneurysm through a catheter to be expelled and expanded to form a bridge isolating the aneurysm from the flow of blood.

Certain other prior art devices contemplate the use of both a graft or stent and foreign bodies, the combination of which are used to repair an aneurysm. In such a system, the foreign bodies are placed within the aneurysm sac and the graft or stent is employed to retain the foreign material within the sac as well as to provide a passage for fluid flow. Due to the complexity of such systems, it is necessary to coordinate the sequence of deployment of the subcomponents of the system. To wit, the foreign bodies must be placed within the aneurysm sac prior to the placement of the graft or stent. Alternatively, in the event the graft or stent is first implaced at the repair site, the graft or stent must be provided with sidewall apertures or spaces through which the foreign material can be advanced to thereafter be placed within the aneurysm sac.

Although potentially successful in such applications as abdominal aortic aneurysms, certain of the prior devices do present a few drawbacks, especially in applications such as intracranial aneurysms. Among the more notable of the difficulties presented is the need to load such devices within a very small delivery catheter lumen and advance the same through typically tortuous pathways. In addition, the longer the graft emplaced at the repair site the larger the surface area for clot formation and endothelial cell growth, which in extreme situations can cause new complications for the patient. Also, such devices do not embody the ability to be deployed, detached and/or retrieved as would be necessary in the intra-cranial vessels. The risks posed by these devices increase in magnitude when the end organ is the brain, with its smaller vessel diameters, weaker vessel walls, and increasingly tortuous paths. The devices described above are thus less than ideally suited to intracranial intravascular intervention.

Moreover, any device placed in the parent artery of an intracranial aneurysm runs the risk of occluding perforating side branches. These perforators are small, usually less than 200 microns in diameter, and can be the sole source of blood flow to important tissues of the brain. Presently known devices such as vascular grafts and stents may partially or completely block the flow of blood to one or more such perforators, thereby causing clinically significant ischemic strokes.

Accordingly, what has been needed is a device for treating hollow spaces that has applications within narrow and highly tortuous vasculature characterized by having numerous perforators. The device should embody structure that not only creates a strong framework across an opening to the target space, but also should provide effective coverage of the opening. The present invention satisfies these needs.

SUMMARY OF THE INVENTION

Briefly and in general terms, the present invention is directed toward devices for treating defects in body lumens such as aneurysms. In one aspect, the devices of the present invention are intended to be placed intrasaccularly (i.e., in the aneurysm). The intrasaccular devices include structure that provides a strong framework as well as improved coverage across the neck of an opening such as into an aneurysm.

In another aspect, the intrasaccular device of the present invention is contemplated to be used in conjunction with foreign bodies such as embolic coils for the purpose of facilitating clotting within an aneurysm sac. The intrasaccular device of the present invention embodies structure for retaining the foreign bodies within the aneurysm sac as well as members for positioning across the opening to the aneurysm sac.

In yet another aspect, the intrasaccular device is formed from a monolithic structure that includes longitudinally extending members. The longitudinally extending members enhance the strength and ability of the device to retain foreign bodies within an aneurysm sac.

In one presently preferred embodiment, the intrasaccular device is formed from a small diameter tube with longitudinal slots that extend nearly the length of the device. As the ends of the device are moved axially toward each other, the intrasaccular device assumes a generally globe shape with the uncut ends or connecting structure forming poles. The intrasaccular device is self-expanding and is treated to assume the globe shape when unconstrained.

In other embodiments, the ends of the intrasaccular device of the present invention includes three or more arms extending from a pole. It is also contemplated that at least at one of the ends of the device, the members define a cruciform shape or assume a spiral configuration and that further includes connecting structure in the form of a perpendicular cylindrical nub at an intersection of the members. In still further embodiments, the connecting structure or nubs at the ends of the device are intended to be inverted. It is also contemplated that only one end of the intrasaccular device of the present invention includes such connecting structure.

One or more of the intrasaccular devices may be deployed within an opening such as an aneurysm sac. At least one of the polar regions of the device are configured to occupy radial space within an entrance to the aneurysm sac as well as embody structure for aligning multiple devices within the sac.

These and other objects and advantages of the invention will become apparent from the following more detailed description, when taken in conjunction with the accompanying drawings of illustrative embodiments.

DETAILED DESCRIPTION OF THE PREFERRED EMBODIMENTS

Figure 1:
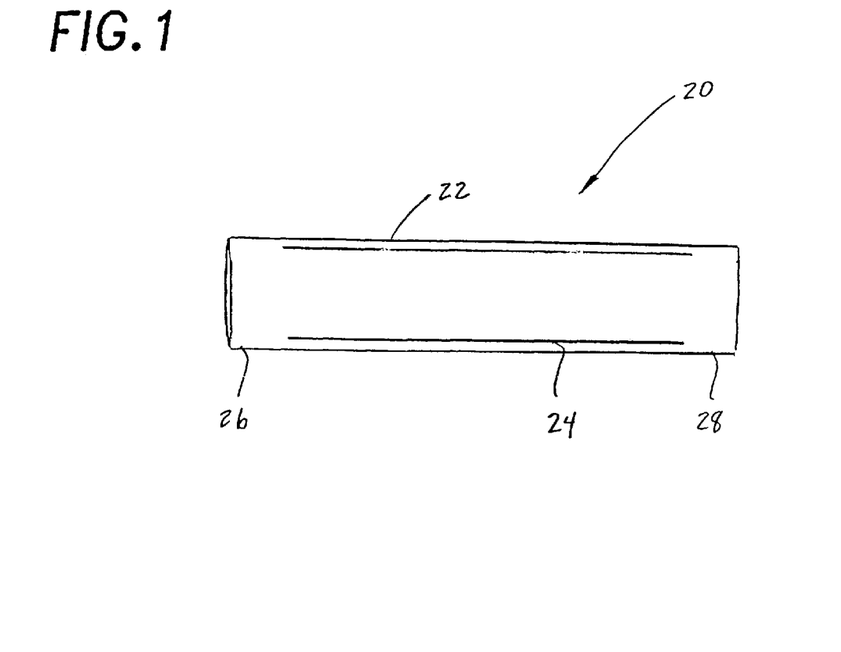
FIG. 1 is a side view of a compressed intrasaccular device of the present invention, depicting a tube with longitudinal slits formed therein.
Figure 2:
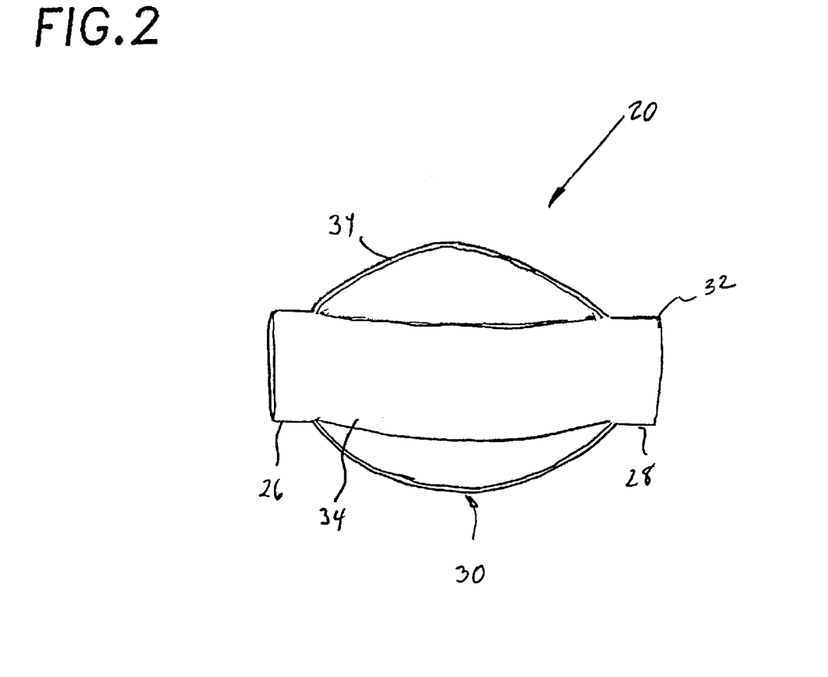
FIG. 2 is a side view, depicting the device of FIG. 1 in an expanded configuration.
Figure 3:
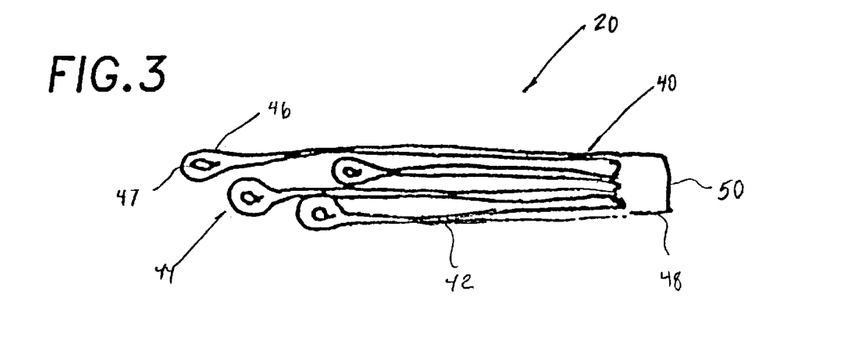
FIG. 3 is a side view, depicting a constrained form of an alternative embodiment of the intrasaccular device of the present invention.
Figure 4:
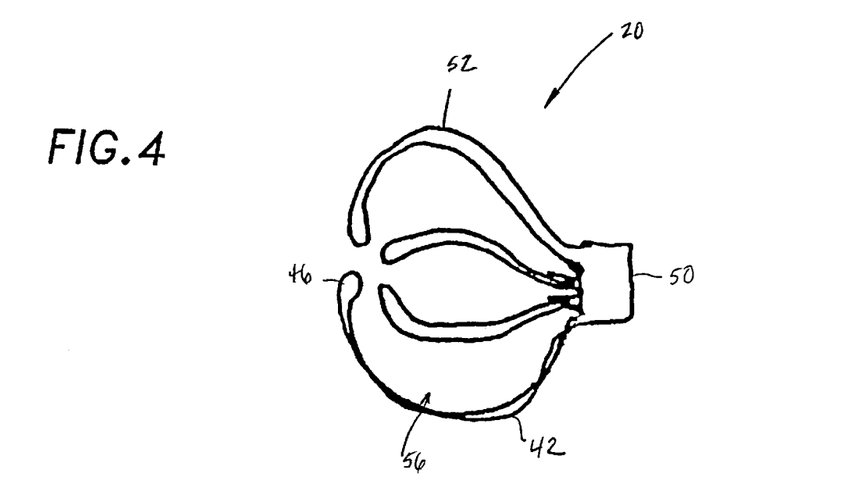
FIG. 4 is a side view, depicting the device of FIG. 3 in an expanded state.

Referring now to the drawings, and specifically to FIGS. 1 and 2, there is shown one embodiment of an intrasaccular device of the present invention. The intrasaccular device of the present invention is particularly suited for treating hollow spaces found within a patient's body. In particular, the intrasaccular devices are adapted for facilitating the repair of aneurysms formed in sidewalls of vasculature as well as at bifurcations or terminal ends of vasculature. The devices include structure that provides an effective framework and coverage across an opening to the aneurysm sac. Moreover, due to their novel design, the intrasaccular devices of the present invention are useful in treating highly tortuous and narrow vasculature such as the neurovasculature.

In one aspect of the present invention, intrasaccular device 20 has a monolithic body formed from a tube 22. The tube 22 has a plurality of parallel slits or slots 24 extending longitudinally substantially the length of the tube 22. End portions 26, 28 of the tube do not include slits 24.

The intrasaccular device 20 is contemplated to be composed of heat setable resilient material such that in its unconstrained state, the device 20 assumes an expanded configuration. That is, as the ends 26, 28 of the device are brought axially closer to each other, a midsection 30 of the intrasaccular device 20 increases in diameter. In one presently preferred embodiment, the midsection 30 of the intrasaccular device 20 assumes a generally spherical or globe-shaped cage with the ends 26, 28 defining poles or perpendicular cylindrical nubs 32. Although the Figures depict a device having a midsection cage 30 with four longitudinally extending members, as few as three or six or more members 34 are contemplated.

As will be developed in more detail below, the constrained tubular shape as well as the self-expandable nature of the intrasaccular device 20 provides a number of advantages. In particular, when compressed into a tubular configuration, the device 20 can be placed within a simple small diameter delivery catheter for advancement within the vasculature. Upon reaching a repair site, the intravascular device 20 is deployed through the delivery catheter and allowed to self-expand at the target site to a desired degree, thereby generally assuming the shape of the cavity at the repair site.

In another aspect of the invention (FIGS. 3–6), the intrasaccular device 20 is formed from a tube 40 that has a plurality of longitudinally extending arms 42 cut into the tube 40. The arms 42 can have varying lengths and widths depending upon the intended application or may have equal lengths and widths. At a terminal end 44 of the arms 40, there may be configured an enlarged cross-sectional area 46. The enlarged ends 46 facilitate reducing "point pressure" and thereby may reduce trauma to vasculature. Staggering the enlarged ends 46 can also allow for better packing. The enlarged area 46 may further include apertures 47 centered therein. The apertures 47 are intended to aid in manufacturing certain embodiments of a cage midsection portion and reduce possible trauma. The ends can also be configured with platinum marker coils (not shown). Each arm 40 projects longitudinally from an uncut portion 48 of the tube 40. The uncut portion 48 forms connecting structure in the form of a pole or perpendicular cylindrical nub 50.

As with the previous described embodiment, the assembled form of this second embodiment of the intrasaccular device 20 includes a midsection 52 that assumes an expanded configuration when unconstrained. As such, the device is self-expandable. A generally cylindrical or a globe-shaped midsection 52 is desirable for certain applications, however, other shapes may be employed for a particular purpose. Thus, the intrasaccular device 20 is heat set to achieve the desired expanded configuration.

In a presently preferred embodiment (FIG. 4), the midsection 52 can be defined by four curved arms 42 forming a cage 56. The cage 56 is bounded on one end by connecting structure or the cylindrical nub 50 and at the other by the terminal ends 46 of the arms 42. The terminal ends 46 may be affixed to one another or alternatively, the ends can remain free floating but generally arranged in close proximity. As before, the device 20 can be constrained to assume a generally tubular profile for advancement through and delivery within vasculature at a repair site.

Figure 5:
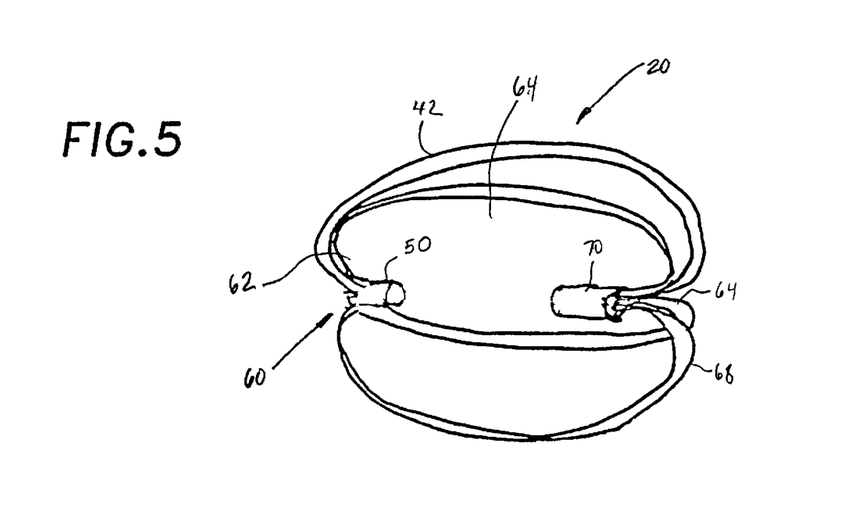
FIG. 5 is a side view, depicting the device of FIG. 3 in an inverted assembled state.

With specific reference to FIG. 5, it is to be understood that in certain circumstances, it may be desirable to configure the intrasaccular device 20 such that it embodies an inverted nub arrangement 60. That is, rather than projecting longitudinally from the connecting structure or nub 50 in a continuous manner, the arms 42 are heat-set so that they each reverse direction and enclose the nub 50 within a first end 62 of a cage 64 defined by the arms 42. Terminal end portions 66 of each arm include a second reversal of direction 68 to complete the midsection cage 64. In the event the device 20 includes free ends, a fixation device 70 is provided to retain the terminal ends 60 of the arms 42 in close proximity. Alternatively, the fixation device 70 can be defined or replaced by a second nub having structure similar to nub 50.

Figure 6:
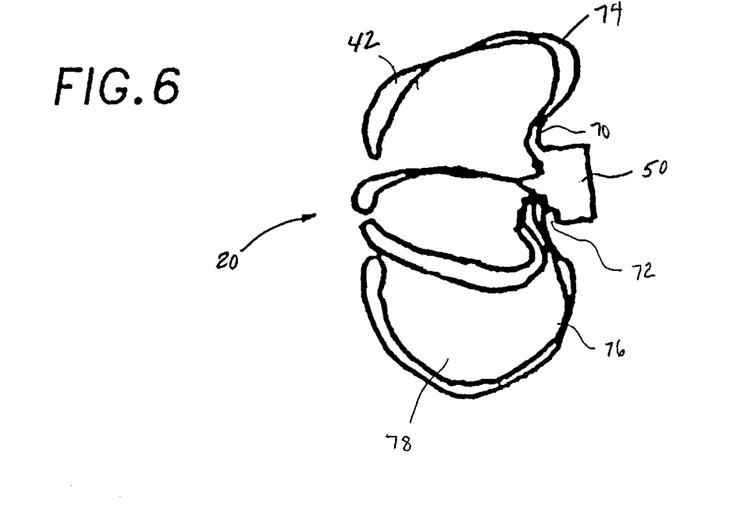
FIG. 6 is a side view, depicting the device of FIG. 4 in a deformed state with a recessed nub.

As shown in FIG. 6, it may also be necessary to recess the connecting structure or nub 50 to provide a desired end profile. To wit, the arms 42 are heat-set so that they are routed through a first reversal of direction 70 where the arms 42 immediately extend from the nub 50. The first reversal of direction defines a recess 72 about the cylindrical nub 50. The arms are then formed to assume a second reversal of direction 74 to thereby form an S-shape with the first reversal of direction and to provide a base portion 74 of a midsection cage 78 adjacent the cylindrical nub 50. The arms 42 continue to extend in a curved fashion to define a generally spherical or a globe-shaped cage 78.

Figure 7:
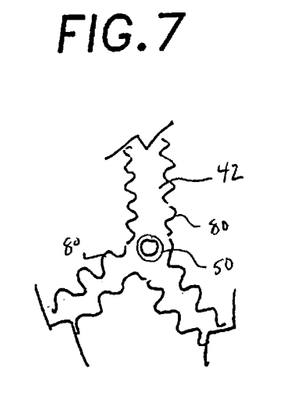
FIG. 7 is a partial end view, depicting wavy members defining an intrasaccular device of the present invention.
Figure 8:
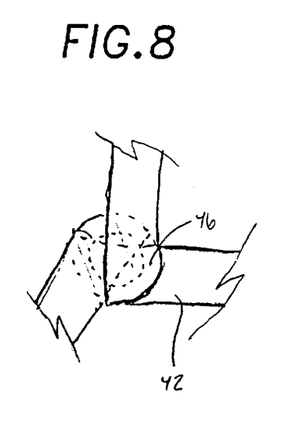
FIG. 8 is a partial end view, depicting one manner of folding members of an intrasaccular device of the present invention.
Figure 9:
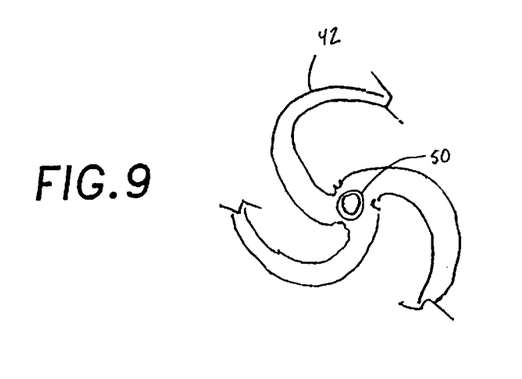
FIG. 9 is a partial end view, depicting members of an intrasaccular device of the present invention configured into a spiral.

With reference to FIGS. 7–9, there are various forms that the members 42 defining the midsection cage of an intrasaccular device 20 can assume. It is contemplated that the members 42 can include edges 80 characterized by waves. Such waves may enhance the flexibility of the member 42 as well as its capacity to retain foreign bodies within an aneurysm sac. In this or other contemplated embodiments, the terminal ends 46 of the members, as stated, can be affixed to each other as shown in FIG. 8 by a simple spot weld which is used to form a "tri-fold" of arms extending from the connecting structure or nub 50. Additionally, as shown in FIG. 9, the members 42 can assume a clockwise or counterclockwise spiral configuration, to thereby provide a cruciform arrangement that is particularly suited for retaining foreign bodies within a cavity. By combining a device that embodies clockwise spirals with a device that embodies counterclockwise spirals, a crossing mesh is formed.

Figure 10:
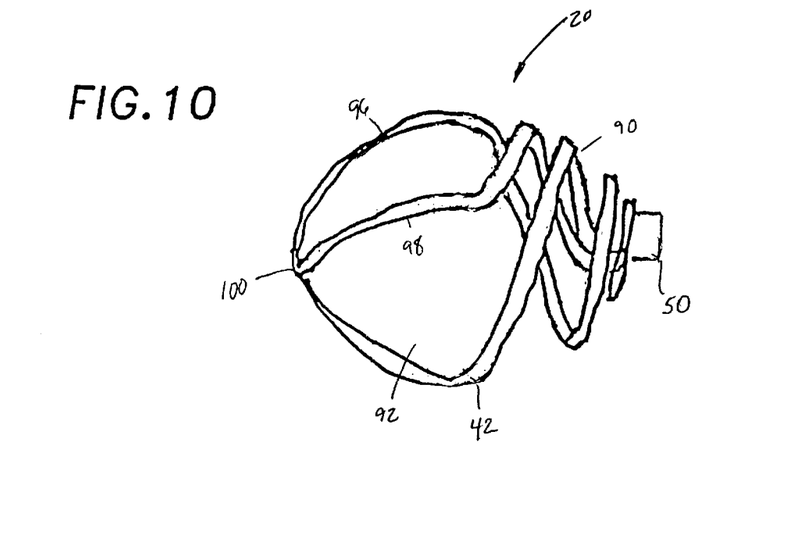
FIG. 10 is a side view, depicting an alternative embodiment of an intrasaccular device of the present invention.

Another presently preferred embodiment of the intrasaccular device 20 of the present invention is shown in FIG. 10. In this embodiment, the members 42 project in a spiral fashion from the cylindrical nub 50. The spiral configuration defines a first portion 90 of a cage 92. The second portion 94 of the cage 92 is defined by curvilinear but generally longitudinally straight or non-spiral portions 98. A generally closed end 100 of the device is formed by the terminal ends of the members 42. The cage 92 of this embodiment is also self-expanding and defines a substantially spherical or globe-shape. The cage can include three to six or more members depending upon the application. When constrained, the device can assume a relatively small diameter profile for loading into a delivery catheter.

As stated, the intrasaccular device 20 of the present invention is heat-set so that the cage midsection assumes a desired profile. It is contemplated that the cage can assume conical, cylindrical as well as other complex forms in addition to a generally spherical shape. Acceptable materials for the intrasaccular device 20 include nitinol, platinum, stainless steel, Eligloy or acceptable polymers or other highly elastic materials. Although it is contemplated that the intrasaccular device 20 be manufactured from a tube using such methods as laser cutting, it is also possible to fabricate the device from a flat sheet, which is then rolled to form a cylindrical nub at least at one end of the device. Moreover, it is additionally contemplated that the intrasaccular device can be coated or covered with a membrane forming polymer that can assist in excluding blood flow. As such, a web may be formed between each or selected members defining the intrasaccular device.

Figure 11:
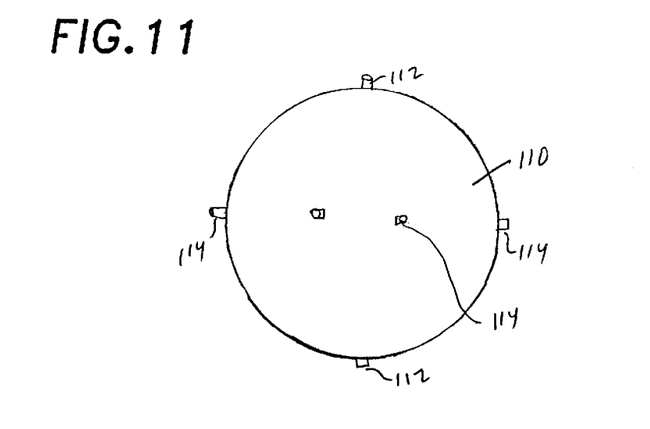
FIG. 11 is a side view, depicting a shaping mandrel.
Figure 12:
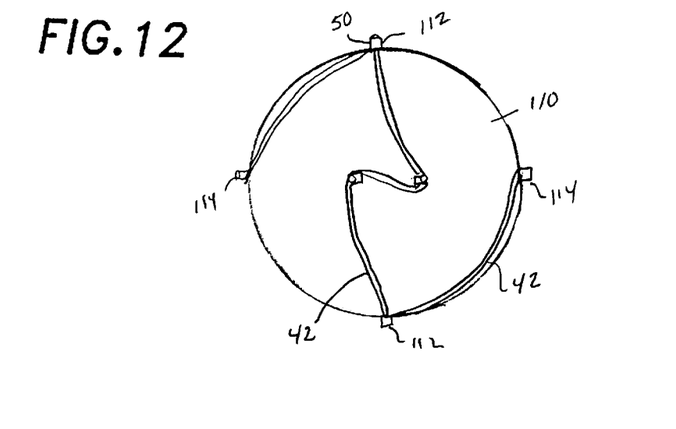
FIG. 12 is a side view, depicting one embodiment of an intrasaccular device of the present invention being manufactured using the shaping mandrel of FIG. 11.

Once a desired pattern for the intrasaccular device is manufactured, the pattern can be placed upon a forming apparatus 110 (FIGS. 11–12). The forming apparatus 110 may have a spherical shape when it is desired that the resultant intrasaccular device 20 be spherical or may have other shapes depending upon the contemplated application. The forming apparatus 110 includes locating pins 112 and forming pins 114. It is to be recognized that the positions of the locating and forming pins 112, 114 can be arranged in various ways to achieve a desired result. The nub 50 of the intrasaccular device being fabricated is placed on a locating pin 112 and arms 42 are deformed about the forming pins 114. The forming pins 114 are positioned on the forming apparatus 110 to aid in consistently and repeatedly deforming the arms 42 to thereby create a desired midsection cage. The forming apparatus 110 with the intrasaccular device 20 mounted thereon is then subjected to heat treating to set the desired shape.

In use, an intrasaccular device 20 of the present invention may be implaced at a repair site using a delivery catheter 120 (See FIGS. 13–16). The delivery catheter 130 may be composed of a simple flexible, elongate tube having an internal bore or lumen 122. The intrasaccular device 20 is compressed to a reduced diameter and inserted within the internal bore 122 of the delivery catheter 120 proximate a terminal end portion 124 of the delivery catheter 120. The terminal end portion 124 may be curved to aid in successfully orienting the INTRASACCULAR device 20 at the repair site. Additionally, radiopaque markers (not shown) may be employed to facilitate placement of the delivery catheter proximate the desired target. Such markers are contemplated to be placed at the terminal ends of the arms of the device 20 or attached or formed as part of the nub thereof.

Figure 13:
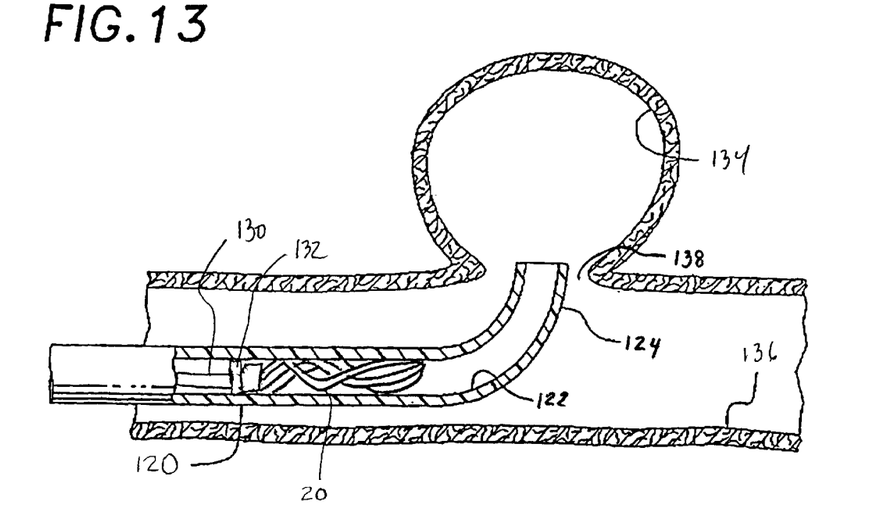
FIG. 13 is a side view partially in cross-section, depicting a delivery catheter containing one embodiment of the intrasaccular device of the present invention, the combination positioned adjacent a repair site.

The intrasaccular device 20 may be releasably attached by conventional means such as a fracturable weld to a pusher member 130. Alternatively, the pusher member 130 can be disconnected from the intrasaccular device 120 and include an enlarged pusher head 132 for engaging an inferior end of the intrasaccular device 20. In either case, the pusher member 130 and pusher head 132 have an exterior profile adapted for being slidably received within the lumen 122 of the delivery catheter 120.

Once an aneurysm or other open space 134 is diagnosed as existing within a body, the delivery catheter 120 is placed within the subject's vasculature 136. Conventional methods such as the Seldinger technique is used to gain access to the patient's vasculature. The intrasaccular device assembly is then advanced through the delivery catheter within the patient's vasculature and to the repair site.

Figure 14:
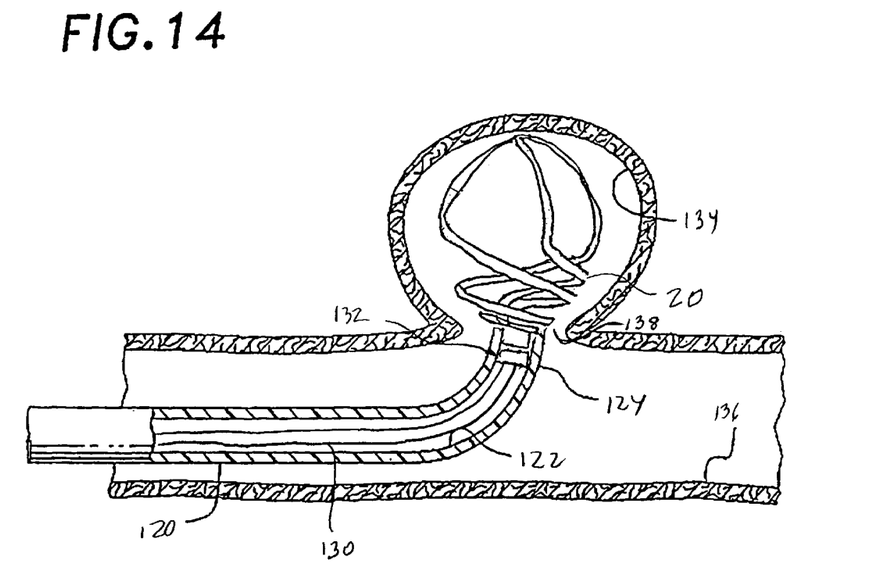
FIG. 14 is a side view partially in cross-section, depicting the intrasaccular device of FIG. 13 being deployed at the repair site.

At the repair site, the delivery catheter 120 is manipulated so that its terminal end portion 124 is adjacent an entrance or opening 138 to the repair site 134. The pusher member 130 is then advanced while holding the delivery catheter 120 stationary. This action causes the intrasaccular device 20 to advance within the delivery catheter 120 toward the terminal end portion 124 of the delivery catheter 120. Alternatively, the catheter is placed at the aneurysm and the device 20 is "unsheathed" by retracting the catheter while holding position with the delivery wire.

Figure 15:
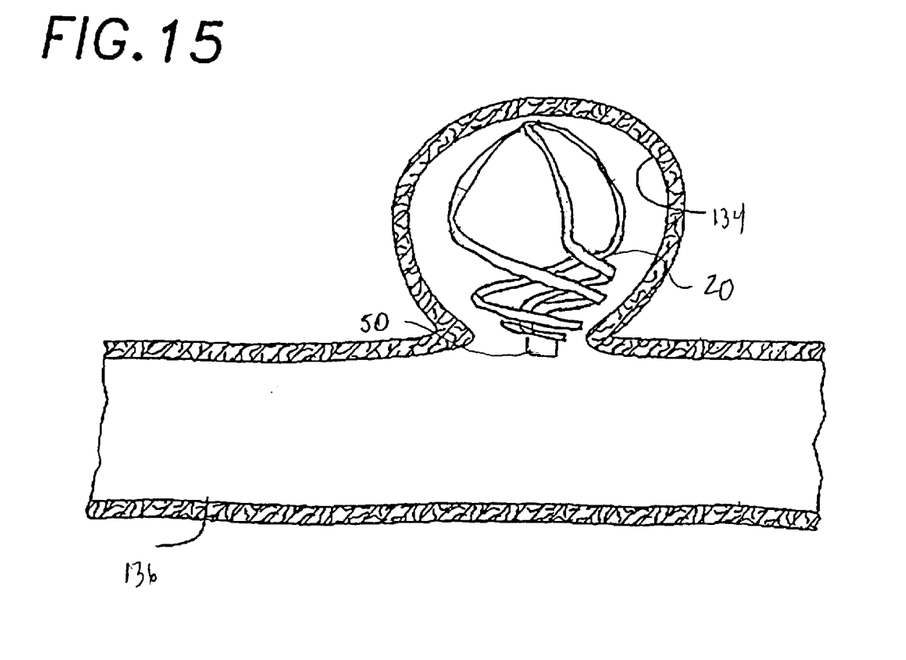
FIG. 15 is a side view partially in cross-section, depicting the device of FIG. 14 after deployment at the repair site.

The pusher 130 is moved longitudinally until the intrasaccular device 20 is deployed from the terminal end portion 124 of the delivery catheter 120 and within the repair site 134. As the intrasaccular device 20 is ejected from the delivery catheter 120, the midsection of the intrasaccular device self-expands to thereby substantially conform to the interior geometry of the saccular repair site. In the event the intrasaccular device 20 is releasably attached to the pusher member 130, action is taken to break the connection. Otherwise, the pusher member 130 is simply advanced until the intrasaccular device 20 has self-expanded within the repair site 134.

When positioned within the repair site 134, the nub 50 of an intrasaccular device is oriented within the opening 138 to the repair site 134. Thereafter, additional intrasaccular devices 20 can be similarly placed within the saccular repair site 134. As specifically shown in FIG. 16, the connecting structure in the form of nubs or poles 50 of the plurality of intrasaccular devices 20 cooperate in aligning adjacent members 42 defining the intrasaccular device 20. The members 42 themselves additionally provide a strong framework across the opening 138 through the repair site 134. Moreover, where an embodiment of the intrasaccular device 20 embodies spirally oriented members in opposite directions for example, an increased amount of coverage across an entrance to the repair site is provided.

Figure 16:
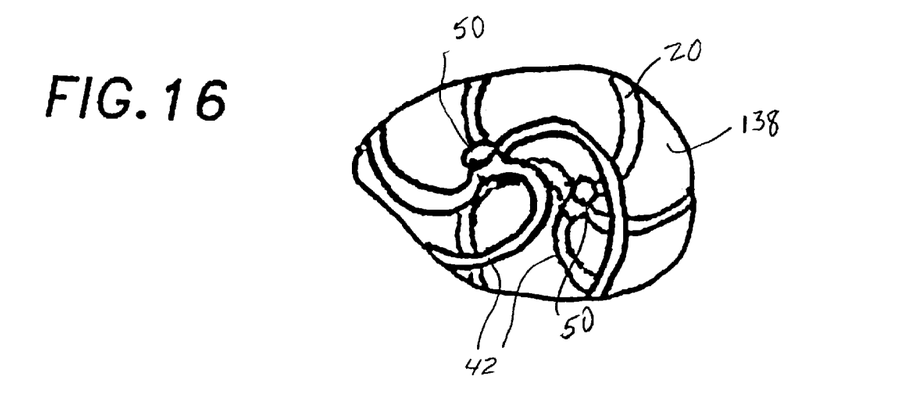
FIG. 16 is a bottom view of an opening to a repair site, depicting a plurality of aligned intrasaccular devices.

Upon successfully delivering the desired number of intrasaccular devices 20 at a repair site, coils (not shown), embolic material, or other foreign bodies may be placed within the repair site to aid in clotting the area. Such material can be inserted through adjacent members 42 defining the intrasaccular device 20. Additional intrasaccular devices 20 may then be placed within the repair site if desired. It is to be recognized, however, that the intrasaccular devices themselves may be relied upon to create thrombosis or change the flow path of blood. As such, it may not be necessary to use the intrasaccular devices 20 in combination with coils or other bodies in every situation.

Thus, the present invention is useful in providing an improved system for repairing abnormalities existing within vasculature. Due to its ability to be compressed into a small profile and subsequently self-expand to provide a framework across an opening to the repair site, the present invention is particularly suited for repairing very distal and tortuous vasculature.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A device for insertion in a saccular cavity of a patient, comprising:

a body formed from a tubular member, the body including a first end, a second end and a midsection, the body further including a cage having an interior, each of the first and second ends configured within the interior of the cage; and wherein the body is expandable from a reduced profile to an expanded profile, the reduced profile suited for insertion into the saccular cavity and the expandable profile defined at least in part by the saccular cavity.

2. The device of claim 1, wherein the body assumes a generally spherical profile when expanded.

3. The device of claim 1, wherein the midsection assumes a generally spherical profile when the body assumes the expanded profile.

4. The device of claim 1, wherein the body is self-expandable.

5. The device of claim 1, further comprising connecting structure formed at the first end.

6. The device of claim 1, further comprising connecting structure formed at the second end.

7. The device of claim 1, the first end further comprising a cylindrical nub and the midsection further comprising a plurality of longitudinally extending members, the longitudinally extending members each having a terminal end.

8. The device of claim 7, wherein the second end of the body is defined by the terminal ends of the plurality of longitudinally extending members.

9. The device of claim 8, wherein the terminal ends of the plurality of longitudinally extending members are affixed to each other.

10. The device of claim 1, the first end further comprising connecting structure, the connecting structure being recessed in the body.

11. The device of claim 1, the first end further comprising connecting structure, the connecting structure having a first portion and a second portion, the midsection further comprising a plurality of deformable members arranged to form a cage, each deformable member having a first terminal end and a second terminal end, the first portion of the connecting structure being attached to each of the first terminal ends of the deformable members.

12. The device of claim 11, wherein the connecting structure is configured within the interior of the cage.

13. The device of claim 1, wherein a plurality of members extend generally longitudinally.

14. The device of claim 1, the body further comprising connecting structure that is adapted to be positioned at an opening to the saccular cavity, the connecting structure facilitating an even distribution within the saccular cavity.

15. The device of claim 1, the first end further comprising a plurality of members, the members providing a strong framework across an opening to the saccular cavity.

* * * * *